(12) United States Patent
Wang et al.

(10) Patent No.: US 10,293,045 B2
(45) Date of Patent: *May 21, 2019

(54) STABLE LIQUID FORMULATIONS OF RECOMBINANT FUSION PROTEINS

(71) Applicant: INNOVENT BIOLOGICS, INC., Suzhou, Jiangsu (CN)

(72) Inventors: Yinjue Wang, Jiangsu (CN); Junfeng Li, Jiangsu (CN); Xiaole Huang, Jiangsu (CN)

(73) Assignee: INNOVENT BIOLOGICS, INC., Jiangsu (CN)

( * ) Notice: Subject to any disclaimer, the term of this patent is extended or adjusted under 35 U.S.C. 154(b) by 171 days.

This patent is subject to a terminal disclaimer.

(21) Appl. No.: 15/513,537

(22) PCT Filed: Sep. 25, 2015

(86) PCT No.: PCT/CN2015/090777
§ 371 (c)(1),
(2) Date: Mar. 23, 2017

(87) PCT Pub. No.: WO2016/045626
PCT Pub. Date: Mar. 31, 2016

(65) Prior Publication Data
US 2019/0038746 A1    Feb. 7, 2019

(30) Foreign Application Priority Data

Sep. 25, 2014  (CN) .......................... 2014 1 0497937

(51) Int. Cl.
| | | |
|---|---|---|
| A61K 38/00 | (2006.01) |
| A61K 38/16 | (2006.01) |
| C07K 14/00 | (2006.01) |
| C07K 14/475 | (2006.01) |
| C07K 14/71 | (2006.01) |
| A61K 39/395 | (2006.01) |
| A61K 47/18 | (2017.01) |
| A61K 47/26 | (2006.01) |
| A61K 38/17 | (2006.01) |
| A61K 9/00 | (2006.01) |
| A61K 9/08 | (2006.01) |
| A61K 31/711 | (2006.01) |
| A61K 47/02 | (2006.01) |
| A61K 47/10 | (2017.01) |
| A61K 47/12 | (2006.01) |
| A61K 47/22 | (2006.01) |
| C07K 16/28 | (2006.01) |

(52) U.S. Cl.
CPC ...... *A61K 39/39591* (2013.01); *A61K 9/0019* (2013.01); *A61K 9/08* (2013.01); *A61K 31/711* (2013.01); *A61K 38/179* (2013.01); *A61K 47/02* (2013.01); *A61K 47/10* (2013.01); *A61K 47/12* (2013.01); *A61K 47/18* (2013.01); *A61K 47/183* (2013.01); *A61K 47/22* (2013.01); *A61K 47/26* (2013.01); *C07K 16/2863* (2013.01); *C07K 16/2896* (2013.01)

(58) Field of Classification Search
None
See application file for complete search history.

(56) References Cited

U.S. PATENT DOCUMENTS

2007/0237758 A1  10/2007  Barry et al.

FOREIGN PATENT DOCUMENTS

| CN | 101312744 A | 11/2008 |
|---|---|---|
| CN | 103212075 A | 7/2013 |
| EP | 3199555 A1 | 8/2017 |
| WO | 2006/104852 A2 | 10/2006 |
| WO | 2007/062040 A1 | 6/2007 |
| WO | WO-2013082563 A1 | 6/2013 |

OTHER PUBLICATIONS

Wells, 1990, Biochemistry 29:8509-8517.*
Ngo et al., 1994, The Protein Folding Problem and Tertiary Structure Prediction, pp. 492-495.*
Supplementary European Search Report corresponding to EP15845094 completed Oct. 20, 2017; 3 pages.
International Preliminary Report on Patentability with Annex (Article 34 Amendments) corresponding to PCT/CN2015/09077 dated Mar. 1, 2017 (CN Version and English Translation); 14 pages.
International Search Report dated Dec. 28, 2015 for PCT/CN2015/090777 filed Sep. 25, 2015, 7 pages (with English translation).

* cited by examiner

Primary Examiner — Christine J Saoud
Assistant Examiner — Jon M Lockard
(74) Attorney, Agent, or Firm — Mintz, Levin, Cohn, Ferris, Glovsky and Popeo, P.C.

(57) ABSTRACT

Provided is a liquid formulation that enables the stable storage of recombinant fusion proteins, comprising a recombinant fusion protein, a buffer salt, a stabilizer, and a surfactant.

13 Claims, No Drawings
Specification includes a Sequence Listing.

STABLE LIQUID FORMULATIONS OF RECOMBINANT FUSION PROTEINS

TECHNICAL FIELD

The present invention belongs to the field of biotechnical pharmaceutical formulations, and in particular relates to stable recombinant fusion protein formulations, preparing methods and use thereof.

REFERENCE TO A "SEQUENCE LISTING"

The Sequence_Listing.txt, created on Mar. 22, 2017, 24,000 bytes, machine format IBM-PC, MS-Windows operating system, is hereby incorporated by reference in its entirety for all purposes.

BACKGROUND ART

Age-related macular degeneration (AMD), also known as senile macular degeneration, is a senescent change of the retinal macular structure, and mainly is irreversible decrease or loss of vision caused by retinal pigment epithelial cells and retinal degeneration. The disease is clinically divided into dry (atrophic) AMD and wet (exudative) AMD, of which, wet AMD accounts for about 20% of the total number of AMD cases. But in western countries, wet AMD is the main reason of blindness for the aged. Intraocular abnormal vascular proliferation is one of the main causes of the occurrence and development of wet AMD, and blocking abnormal vascular proliferation is the basis of treatment of wet AMD. It may slow down or even prevent the disease process. Vascular endothelial growth factor (VEGF) is a secretory protein that can induce angiogenesis, increase vascular permeability, and cause inflammation. And these factors are closely related to the development of wet AMD. Therefore, in the development of medicaments for treating wet AMD, VEGF is a potential therapeutic target.

Recombinant fusion protein of human vascular endothelial growth factor receptor-antibody-human complement receptor 1 (hereinafter referred to as IBI302) is a macromolecule designed and developed for AMD disease based on the above mechanism. It is a new drug of State Category I with global intellectual property designed by the applicant. The route of administration is designed for intravitreal injection, and the dose is expected to be 0.5~2 mg/eye.

Since 1982, after the introduction of the first recombinant drug (artificial insulin), more and more recombinant fusion protein drugs have been developed by protein engineering technology. Some of them have been accepted as conventional drugs. However, because such drug is a polypeptide or protein with large molecular weight, its performance is very unstable, prone to deterioration, and very likely to self-aggregation under high concentration of the protein. These unfavorable factors make a great challenge to making these drugs into stable, safe and effective formulations.

Recombinant fusion protein is a biomacromolecule, structure of which is very complex. During production and storage process, a variety of physical and chemical changes will occur in the expressed protein molecules. Physical changes are: adsorption, unfolding denaturation, aggregation and precipitation. Chemical changes are: deamidation, isomerization, oxidation and so on. These changes may influence the safety and effectiveness of the final product. Therefore, it is important to establish a suitable formulation to protect the stability and safety of the product.

IBI302 is a double-target specific fusion protein and is a new drug of State Category I. Due to its complex structure, the protein is unstable in chemical properties, and is prone to aggregation and the charge isomers are easily converted from the alkaline component to the acidic component.

Therefore, there is still a need in the art to develop recombinant protein formulation for protecting the stability of the product.

SUMMARY OF INVENTION

One object of the present invention is to provide a recombinant fusion protein formulation, which can stabilize the fusion protein at a higher concentration. In addition, the formulation can maintain its stability under conditions of high temperature acceleration, long term refrigeration and repeated freezing and thawing, thereby improving the clinical use safety.

In the first aspect of the present invention, a liquid formulation of a recombinant fusion protein is provided, which comprises a recombinant fusion protein, a buffer salt, a stabilizer, a surfactant and sterile water for injection, wherein, the concentration of the recombinant fusion protein is 5 to 45 mg/mL;

the buffer salt is selected from citrate salt, acetate salt or any combination thereof, and the concentration of the salt is 5 to 25 mmol/L, preferably 8-22 mmol/L;

the stabilizer is selected from sodium chloride, an amino acid or a polyol (polyhydric alcohol) or any combination thereof, wherein the amino acid is selected from arginine, glycine, histidine or any combination thereof, and the polyol is selected from sucrose, sorbitol, mannitol or any combination thereof; and the concentration of sodium chloride is 100 to 200 mmol/L; the concentration of amino acid is 50 to 350 mmol/L; and the concentration of polyol is 1-15 wt %, based on total weight of the liquid formulation;

the surfactant is selected from polysorbate 20, polysorbate 80, poloxamer 188, or any combination thereof and the concentration of the surfactant is 0.01-0.08 wt %, based on total weight of the liquid formulation;

and the pH of the liquid formulation is from 4.5 to 7.5.

In another preferred embodiment, the recombinant fusion protein is a recombinant fusion protein of human vascular endothelial growth factor receptor-antibody-human complement receptor 1, amino acid sequence of which is set forth in SEQ ID NO: 1 or SEQ ID NO: 4.

In another preferred embodiment, the stabilizer is selected from an amino acid, polyol and any combination thereof.

In another preferred embodiment, the concentration of sodium chloride is 120 to 180 mmol/L.

In another preferred embodiment, the concentration of amino acid is 70 to 260 mmol/L.

In another preferred embodiment, the concentration of polyol is 3-10 wt %.

In another preferred embodiment, the concentration of polyol is 200 to 300 mmol/L, preferably of 220 to 270 mmol/L.

In another preferred embodiment, the pH of the liquid formulation is from 5.0 to 7.2, preferably is from 5.5 to 7.0.

In another preferred embodiment, the buffer salt is citrate; the amino acid is arginine; the polyol is sucrose; and the surfactant is polysorbate 20.

In the present invention, the buffer salt is sodium citrate, sodium acetate or a combination thereof.

In the second aspect of the present invention, a kit is provided which comprises a liquid formulation according to the first aspect of the present invention and a container containing the liquid formulation.

Further, the kit further contains an instruction.

In the third aspect of the present invention, a use of the liquid formulation according to the first aspect of the present invention for preparing a medicament for prevention and/or treatment of age-related macular degeneration is provided.

In another preferred embodiment, the age-related macular degeneration is wet age-related macular degeneration.

The liquid formulation of the present invention can keep the recombinant fusion protein stable, so that the recombinant protein can be stably present in the prescription drugs, the quality of the product can be improved, the shelf life is prolonged and the safety of clinical use is improved. The liquid formulation has good thermal stability, and can remain stable in the high temperature acceleration, long-term refrigeration and repeated freezing and thawing conditions.

It should be understood that in the present invention, the technical features specifically described above and below (such as the examples) can be combined with each other, thereby constituting a new or preferred technical solution, which needs not be specified one by one.

DETAILED DESCRIPTION OF INVENTION

Through extensive and intensive researches, the inventors have unexpectedly and firstly discovered a recombinant fusion protein formulation which can keep the product stable under the acceleration, long-term and freeze-thaw conditions. Recombinant fusion proteins (VEGF inhibitors) that can be used in the present invention also include recombinant fusion proteins (VEGF inhibitors) obtained by other genetic engineering techniques. Based on this discovery, the inventors have completed the present invention.

Recombinant Fusion Protein of Human Vascular Endothelial Growth Factor Receptor-Antibody-Human Complement Receptor 1

The preferred recombinant recombinant protein of the present invention is a recombinant fusion protein of human vascular endothelial growth factor receptor-antibody-human complement receptor 1 (see U.S. 61/629,932 (PCT/US2012/067489); title of invention: Protein inhibitors to complement and VEGF pathways and Methods of use thereof); the amino acid sequence of which is set forth in SEQ ID NO: 1.

Another preferred recombinant fusion protein of the present invention is a recombinant fusion protein of human vascular endothelial growth factor receptor-antibody-human complement receptor 1, the amino acid sequence of which is set forth in SEQ ID NO: 4.

Liquid Formulation

The liquid formulation of a recombinant fusion protein of the present invention comprises a recombinant fusion protein, a buffer salt, a stabilizer, a surfactant and sterile water for injection.

In another preferred embodiment, the liquid formulation comprises a recombinant fusion protein, a buffer salt, sodium chloride, a surfactant and sterile water for injection.

In another preferred embodiment, the liquid formulation comprises a recombinant fusion protein, a buffer salt, a polyol, a surfactant and sterile water for injection.

In another preferred embodiment, the liquid formulation comprises a recombinant fusion protein, a buffer salt, an amino acid, a surfactant and sterile water for injection.

In another preferred embodiment, the liquid formulation comprises a recombinant fusion protein, a buffer salt, a polyol, an amino acid, a surfactant and sterile water for injection.

The concentration of recombinant fusion protein is 5 to 45 mg/Ml.

The buffer salt is one or a combination of two or more kinds of citrate salt, and acetate salt, and the concentration of the salt is 5 to 25 mmol/L, preferably of 8-22 mmol/L.

The stabilizer is one or a combination of two or more kinds of sodium chloride, an amino acid and a polyol.

The amino acid is one or a combination of two or more kinds of arginine, glycine, and histidine. The concentration of amino acid is 50 to 350 mmol/L, preferably of 70-260 mmol/L.

The polyol is one or a combination of two or more kinds of sucrose, sorbitol, and mannitol. The concentration of polyol is 1-15 wt %, preferably of 3-10 wt %.

The concentration of sodium chloride is 100-200 mmol/L.

The surfactant is one or a combination of two or more kinds of polysorbate 20, polysorbate 80, poloxamer 188.

The concentration of surfactant is 0.01-0.08 wt %, preferably of 0.02-0.06 wt %, based on total weight of the liquid formulation.

The pH of the liquid formulation is from 4.5 to 7.5, preferably is 5.0-7.0.

The liquid formulation of the present invention or a kit comprising the liquid formulation can be used for the preparation of a medicament for the prevention and/or treatment of age-related macular degeneration. The recombinant protein can be maintained stable, the product can be of high quality and long shelf life and the safety of clinical use is improved.

The features mentioned above, or the features mentioned in the examples, may be combined in any combination. All features disclosed in this specification may be used in conjunction with any form of the composition, and each of the features disclosed in the specification may be substituted by any alternative feature that provides the same, equal or similar purpose. Thus, unless otherwise specified, the features disclosed are only general examples of equal or similar features.

The Main Advantages of the Present Invention Comprise:

(1) The present invention provides a novel formulation with a longer shelf life that allows the recombinant fusion protein, such as the recombinant fusion protein of human vascular endothelial growth factor receptor-antibody-human complement receptor 1 remain stable. The formulation can remain stable under the high temperature acceleration, long-term refrigeration and repeated freezing and thawing conditions.

(2) In the liquid formulation of the present invention, the physicochemical stability of the recombinant fusion protein formulation can be improves, so that the recombinant protein can be stably present in the prescription drug, the quality of the product is improved, the shelf life is prolonged and the safety of clinical use is improved.

The present invention will be further illustrated below with reference to the specific examples. It should be understood that these examples are only to illustrate the invention, not to limit the scope of the invention. The experimental methods with no specific conditions described in the following examples are generally performed under the conventional conditions (e.g., the conditions described by Sambrook et al., Molecular Cloning-A Laboratory Manual Cold Spring Harbor Laboratory Press, 1989), or according to the manufacture's instructions. Unless indicated otherwise, parts and percentage are calculated by weight.

Unless otherwise defined, all professional and scientific terms used herein have the same meaning as those skilled in the art are familiar with. In addition, any method and material similar to or equivalent to the contents described herein may be applied to the method of the present invention. The preferred embodiments and materials described herein are for exemplary purposes only.

General Method

SEC-HPLC method: is performed according to Appendix III B of "Pharmacopoeia of the People's Republic of China" (2010 edition, part three), hydrophilic silica gel size exclusion column is used in detection, and the purity of the sample is calculated with area normalization method.

Charge isomerization (cIEF): the sample was ionized by applying a voltage at both ends of the capillary by using a Beckman capillary electrophoresis (Model: PA800 plus) and a coated capillary Neutral Capillary (50 µm i.d×45 cm). After ionization, the plot was integrated and analysised with 32Karat software, and calculated according to the area normalization method.

DSC: MlcroCal VP-DSC was used, the starting temperature was 10° C., the end temperature was 110° C., and the scanning rate was 60° C./Hr. The final Tm values of each sample were obtained after subtracting the corresponding buffer.

Example 1

The Effect of Amino Acids, Polyols and Sodium Chloride on the Stability of Fusion Protein Various solutions were prepared with sterile injectable water as shown in Table 1, and the fusion protein (amino acid sequence as set forth in SEQ ID NO: 4) was subjected to ultrafiltration substitution with the prepared respective solutions.

The ultrafiltration substitution fluid with the fusion protein concentration of 10 mg/ml was diluted to 1.5 mg/ml with the corresponding solution. Then, 1.5 ml of the dilution was taken and an appropriate amount of polysorbate 20 was added to a final concentration of 0.03% by weight. A sample for detection was obtained after filtration using a 0.2 µm filter.

In addition, 5 ml of the solution described in Table 1 was taken and an appropriate amount of polysorbate 20 was added so that the final concentration thereof was 0.03% and then filtered through a 0.2 µm filter as a buffer blank control. The Tm values for different protein stabilizers were measured by DSC method. The experimental results were shown in Table 2.

TABLE 1

Effects of Different Kinds of Protein Stabilizers on the Stability of Fusion Protein

| No. | Buffer components | Stabilizer | pH Value |
|---|---|---|---|
| 1-1 | 10 mmol/L Sodium citrate | Sucrose 8% by weight | 6.2 |
| 1-2 | | Sorbitol 250 mmol/L | 6.2 |
| 1-3 | | Sodium chloride 150 mmol/L | 6.2 |
| 1-4 | | Histidine 150 mmol/L | 6.2 |
| 1-5 | | Glycine 250 mmol/L | 6.2 |
| 1-6 | | Arginine 150 mmol/L | 6.2 |
| 1-7 | | Arginine 80 mmol/L + Sucrose 5% by weight | 6.2 |
| 2-1 | 10 mmol/L | Sucrose 8% by weight | 6.2 |

TABLE 1-continued

Effects of Different Kinds of Protein Stabilizers on the Stability of Fusion Protein

| No. | Buffer components | Stabilizer | pH Value |
|---|---|---|---|
| 2-2 | Sodium acetate | Sorbitol 250 mmol/L | 6.2 |
| 2-3 | | Sodium chloride 150 mmol/L | 6.2 |
| 2-4 | | Histidine 150 mmol/L | 6.2 |
| 2-5 | | Glycine 250 mmol/L | 6.2 |
| 2-6 | | Arginine 150 mmol/L | 6.2 |
| 2-7 | | Arginine 80 mmol/L + Sucrose 5% by weight | 6.2 |

2: DSC Results of Different Kinds of Protein Stabilizer

| No. | Tm Value (° C.) |
|---|---|
| 1-1 | 57.95 |
| 1-2 | 58.16 |
| 1-3 | 58.51 |
| 1-4 | 58.58 |
| 1-5 | 57.64 |
| 1-6 | 58.60 |
| 1-7 | 58.61 |
| 2-1 | 53.27 |
| 2-2 | 53.25 |
| 2-3 | 57.60 |
| 2-4 | 58.59 |
| 2-5 | 52.32 |
| 2-6 | 58.40 |
| 2-7 | 57.33 |

The final Tm values of the respective samples were obtained by subtracting the corresponding solution blanks from 14 different samples. The results showed that all of 14 samples exhibited high thermal stability. Wherein the thermal stability of sample groups 1-1, 1-2, 1-3, 1-4, 1-5, 1-6, 1-7, 2-3, 2-4, 2-6, 2-7 was the best followed by that of sample groups 2-1, 2-2, 2-5. The results showed that the recombinant fusion protein formulations consisting of components of Table 1 and the recombinant fusion protein exhibited better thermal stability.

Example 2 pH Stability

Solutions of each pH were prepared with sterile injectable water according to Table 3, and the fusion protein (amino acid sequence as set forth in SEQ ID NO: 4) was subjected to ultrafiltration substitution with the prepared solutions.

The ultrafiltration substitution fluid with the fusion protein concentration of 10 mg/ml was diluted to 1.5 mg/ml with the corresponding solution. Then, 1.5 ml of the dilution was taken and an appropriate amount of polysorbate 20 was added to a final concentration of 0.03% by weight. A sample for detection was obtained after filtration using a 0.2 µm filter.

In addition, 5 ml of the solution of each pH value was taken and an appropriate amount of polysorbate 20 was added so that the final concentration thereof was 0.03% and then filtered through a 0.2 µm filter as a buffer blank control. The Tm values for on different pH value were measured by DSC method. The experimental results were shown in Table 4.

TABLE 3

Samples used in pH Stability Example

| No. | pH | Buffer | Stabilizer |
|---|---|---|---|
| 1 | 5.5 | Sodium citrate 10 mmol/L | Arginine 80 mmol/L + Sucrose 5% by weight |
| 2 | 6.0 | Sodium citrate 10 mmol/L | Arginine 80 mmol/L + Sucrose 5% by weight |
| 3 | 6.0 | Sodium acetate 10 mmol/L | Arginine 80 mmol/L + Sucrose 5% by weight |
| 4 | 6.5 | Sodium acetate 10 mmol/L | Arginine 80 mmol/L + Sucrose 5% by weight |
| 5 | 7.0 | Sodium citrate 10 mmol/L | Arginine 80 mmol/L + Sucrose 5% by weight |
| 6 | 7.5 | Sodium citrate 10 mmol/L | Arginine 80 mmol/L + Sucrose 5% by weight |

TABLE 4

DSC results of pH stability

| No. | pH | Tm Value (° C.) |
|---|---|---|
| 1 | 5.5 | 59.58 |
| 2 | 6.0 | 59.89 |
| 3 | 6.0 | 59.75 |
| 4 | 6.5 | 59.87 |
| 5 | 7.0 | 54.85 |
| 6 | 7.5 | 52.75 |

The Tm values of the different samples of 6 groups obtained by subtracting the corresponding buffer showed that the samples 1-4 exhibited high thermal stability followed by sample 5, and the Tm of sample 6 was slightly lower, indicating that the recombinant fusion protein exhibited high thermal stability within pH 5.5-7.0.

Example 3

Formulation of Recombinant Fusion Protein Human Vascular Endothelial Growth Factor Receptor-Antibody-Human Complement Receptor 1

The formulation was prepared according to the following formula and the amino acid sequence of the fusion protein was set forth in SEQ ID NO: 4.

Formulation A

| the recombinant fusion protein | 10 mg/ml; |
|---|---|
| Sodium citrate | 10 mmol/L; |
| Arginine | 80 mmol/L; |
| Sucrose | 5 wt %; |
| Polysorbate 20 | 0.03 wt %; |
| pH | 6.2 |
| Solvent | the sterile water for injection |

Under the sterile condition, the semi-finished product was subpackaged into the vials, and stamped with rubber stoppers and aluminum plastic covers to obtain finished products.

Formulation B

| The recombinant fusion protein | 40 mg/ml; |
|---|---|
| Sodium citrate | 10 mmol/L; |
| Arginine | 80 mmol/L; |
| Sucrose | 5 wt %; |
| Polysorbate 20 | 0.03 wt %; |
| pH | 6.2 |
| Solvent | the sterile water for injection |

Under the sterile condition, the semi-finished product was subpackaged into the vials, and stamped with rubber stoppers and aluminum plastic covers to obtain finished products.

Example 4

Accelerated Stability Experiment

The samples of Example 3 were stored in a 25° C. incubator for accelerated stability experiments. After one month, the samples were taken out and compared with the test results at 0 days to measure the accelerated stability of the formulation under high temperature conditions. The results were shown in Table 5 and Table 6.

TABLE 5

The results of changes in protein charge isomerization at 25° C. ± 2° C. (PI > 8.0)

| Sample name | 0 day | 1 month |
|---|---|---|
| Formulation A (10 mg/ml) | 68.75% | 68.87% |
| Formulation B (40 mg/ml) | 67.82% | 68.45% |

TABLE 6

The results of changes in protein purity at 25° C. ± 2° C. (percentage of SEC main peak)

| Sample name | 0 day | 1 month |
|---|---|---|
| Formulation A (10 mg/ml) | 99.23% | 99.01% |
| Formulation B (40 mg/ml) | 99.03% | 98.51% |

The chemical stability of the recombinant fusion protein was characterized by capillary isoelectric focusing (cIEF) and protein purity (SEC-HPLC). The change in the percentage of isoelectric point PI>8.0 and the content of main peak of protein purity (SEC-HPLC) were used as the determination means. The results showed that the charge isomer content in Formulations A and B did not significantly change after 1 month of accelerated experiment (see table 5). At the same time, the main peak content in the Formulations A and B did not significantly change (see Table 6), while other indicators, such as appearance, protein concentration, turbidity and so on in the accelerated conditions did not significantly change. The results showed that, at 25° C., the recombinant fusion protein in both of two formulations could maintain stabile for at least 1 month.

Example 5

Long-Term Stability Experiment

The sample used in this example was the same as that of Example 4, i.e., the formulation prepared in Example 3. The samples were stored in a 2-8° C. incubator for long-term stability experiments. The samples were taken out at the third and sixth month and compared with the test results at 0 day to measure the Long-term stability of the formulation at low temperature.

The experimental results were shown in Tables 7 and 8.

TABLE 7

The results of changes in protein charge isomerization at 2-8° C. (PI > 8.0)

| Sample name | 0 day | 3 months | 6 months |
|---|---|---|---|
| Formulation A (10 mg/ml) | 56.68% | 56.65% | 55.20% |
| Formulation B (40 mg/ml) | 56.42% | 55.90% | 55.27% |

TABLE 8

The results of changes in protein purity
at 2-8° C. (percentage of SEC main peak)

| Sample name | 0 day | 3 months | 6 months |
|---|---|---|---|
| Formulation A (10 mg/ml) | 99.23% | 99.32% | 99.09% |
| Formulation B (40 mg/ml) | 99.03% | 99.09% | 98.64% |

The results showed that there was no significant change in charge isomerization (cIEF) and protein purity (SEC-HPLC) within 6 months under long-term storage conditions at 2-8° C. While other indicators, such as appearance, protein concentration, turbidity and so on did not significantly change under the acceleration conditions. The results showed that both of two formulations could be stored for at least 6 months under long term conditions.

Example 6

Freeze-Thaw Stability

The sample used in this example was substantially the same as the formulation of Example 3, except that the amino acid sequence of the fusion protein was set forth in SEQ ID NO: 1. The samples were frozen at −80° C. and thawed at room temperature. The samples were repeatedly freeze-thawed for three times or six times. The results were shown in Tables 9 and 10.

TABLE 9

The results of changes in protein charge isomerization
under freeze-thaw conditions (PI > 8.0)

| Sample name | 0 | three times | six times |
|---|---|---|---|
| Formulation A (10 mg/ml) | 65.99% | 65.00% | 64.99% |
| Formulation B (40 mg/ml) | 65.81% | 63.55% | 63.71% |

TABLE 10

The results of changes in protein purity under freeze-thaw conditions (percentage of SEC main peak)

| Sample name | 0 | three times | six times |
|---|---|---|---|
| Formulation A (10 mg/ml) | 99.23% | 99.31% | 99.22% |
| Formulation B (40 mg/ml) | 99.03% | 98.99% | 99.02% |

The results showed that there was no significant change in the charge isomerization (cIEF) and protein purity (SEC-HPLC) for the three groups of sample after freeze-thaw 6 times, and other test indicators, such as appearance, and visible foreign matter related to the physical properties were qualified. The results showed that the physical and chemical properties of the formulation were still stable after freezing and thawing at least 6 times.

The results of the above studies showed that the liquid formulation prepared by using the buffer and the stabilizer of the present invention and the recombinant fusion protein exhibited good stability, and the fusion protein can be stably preserved at a higher concentration. The formulation could remain stable under the high temperature acceleration, long-term refrigeration and repeated freezing and thawing conditions, and the safety of clinical use can be improved.

All documents referred to in the present invention are incorporated by reference as if each reference is cited alone as a reference in the present application. In addition, it should be understood that after reading the teachings of the present invention described above, a skilled person in the art can make various changes or modifications of the invention, and these equivalent forms also fall into the scope as defined by the appended claims of the present application.

The invention claimed is:

1. A liquid formulation of a recombinant fusion protein, which comprises a recombinant fusion protein, a buffer salt, a stabilizer, a surfactant and sterile water for injection, wherein, the recombinant fusion protein has a concentration of 5 to 45 mg/mL;

the buffer salt is citrate salt, acetate salt or any combination thereof, and has a concentration of 5 to 25 mmol/L;

the stabilizer is an amino acid or a combination of a polyol and an amino acid, wherein the amino acid is arginine, and the polyol is sucrose; the amino acid has a concentration of 50 to 350 mmol/L; and the polyol has a concentration of 1-15 wt %, based on total weight of the liquid formulation;

the surfactant is polysorbate 20 and has a concentration of 0.01-0.08 wt %, based on total weight of the liquid formulation;

and the pH of the liquid formulation is from 5.5 to 7.5; and the recombinant fusion protein is a recombinant fusion protein of human vascular endothelial growth factor receptor-antibody-human complement receptor 1 which comprises the amino acid sequence as set forth in SEQ ID NO: 1 or SEQ ID NO: 4.

2. The liquid formulation of claim 1, wherein the recombinant fusion protein is a recombinant fusion protein of human vascular endothelial growth factor receptor-antibody-human complement receptor 1 which has an amino acid sequence as set forth in SEQ ID NO: 1.

3. The liquid formulation of claim 1, wherein the stabilizer is a combination of arginine and sucrose.

4. The liquid formulation of claim 1, wherein the amino acid has a concentration of 70 to 260 mmol/L.

5. The liquid formulation of claim 1, wherein the polyol has a concentration of 3-10 wt %.

6. The liquid formulation of claim 1, wherein the pH of the liquid formulation is from 5.5 to 7.2.

7. The liquid formulation of claim 1, wherein the pH of the liquid formulation is from 5.5 to 7, and the liquid formulation comprises:

| the recombinant fusion protein | 5-45 mg/ml; |
| citrate | 5-15 mmol/L; |
| arginine | 50-100 mmol/L; |
| sucrose | 2-8 wt %; |
| polysorbate 20 | 0.02-0.06 wt %; |
| and the sterile water for injection. | |

8. The liquid formulation of claim 1, wherein the buffer salt is citrate.

9. The liquid formulation of claim 1, wherein the pH of the liquid formulation is from 5.5 to 7.0.

10. The liquid formulation of claim 1, wherein the buffer salt is citrate and has a concentration of from 8 to 22 mmol/L.

11. A kit comprising the liquid formulation according to claim 1 and a container containing the liquid formulation.

12. A method or treating age-related macular degeneration comprising administering to a subject in need thereof the liquid formulation according to claim 1 or the kit according to claim 11.

13. The method of claim 12, wherein the age-related macular degeneration is wet age-related macular degeneration.

* * * * *

SEQUENCE LISTING

```
<160> NUMBER OF SEQ ID NOS: 4

<210> SEQ ID NO 1
<211> LENGTH: 629
<212> TYPE: PRT
<213> ORGANISM: Artificial sequence
<220> FEATURE:
<223> OTHER INFORMATION: Fusion protein

<400> SEQUENCE: 1

Asp Thr Gly Arg Pro Phe Val Glu Met Tyr Ser Glu Ile Pro Glu Ile
1               5                   10                  15

Ile His Met Ala Glu Gly Arg Glu Leu Val Ile Pro Cys Arg Val Thr
            20                  25                  30

Ser Pro Asn Ile Thr Val Thr Leu Lys Lys Phe Pro Leu Asp Thr Leu
        35                  40                  45

Ile Pro Asp Gly Lys Arg Ile Ile Trp Asp Ser Arg Lys Gly Phe Ile
    50                  55                  60

Ile Ser Asn Ala Thr Tyr Lys Glu Ile Gly Leu Leu Thr Cys Glu Asn
65                  70                  75                  80

Thr Val Asn Gly His Leu Tyr Lys Thr Asn Tyr Leu Thr His Arg Gln
                85                  90                  95

Thr Asn Thr Ile Ile Asp Val Val Leu Ser Pro Ser His Gly Ile Glu
```

-continued

```
                100                 105                 110
Leu Ser Val Gly Glu Lys Leu Val Leu Asn Cys Thr Ala Arg Thr Glu
            115                 120                 125
Leu Asn Val Gly Ile Asp Phe Asn Trp Glu Tyr Pro Ser Ser Lys His
        130                 135                 140
Gln His Lys Lys Leu Val Asn Arg Asp Leu Lys Thr Gln Ser Gly Ser
145                 150                 155                 160
Glu Met Lys Lys Phe Leu Ser Thr Leu Thr Ile Asp Gly Val Thr Arg
                165                 170                 175
Ser Asp Gln Gly Leu Tyr Thr Cys Ala Ala Ser Ser Gly Leu Met Thr
            180                 185                 190
Lys Lys Asn Ser Thr Phe Val Arg Val His Glu Lys Asp Lys Thr His
        195                 200                 205
Thr Cys Pro Pro Cys Pro Ala Pro Glu Leu Leu Gly Pro Ser Val
210                 215                 220
Phe Leu Phe Pro Pro Lys Pro Lys Asp Thr Leu Met Ile Ser Arg Thr
225                 230                 235                 240
Pro Glu Val Thr Cys Val Val Asp Val Ser His Glu Asp Pro Glu
                245                 250                 255
Val Lys Phe Asn Trp Tyr Val Asp Gly Val Glu Val His Asn Ala Lys
            260                 265                 270
Thr Lys Pro Arg Glu Glu Gln Tyr Asn Ser Thr Tyr Arg Val Val Ser
        275                 280                 285
Val Leu Thr Val Leu His Gln Asp Trp Leu Asn Gly Lys Glu Tyr Lys
    290                 295                 300
Cys Lys Val Ser Asn Lys Ala Leu Pro Ala Pro Ile Glu Lys Thr Ile
305                 310                 315                 320
Ser Lys Ala Lys Gly Gln Pro Arg Glu Pro Gln Val Tyr Thr Leu Pro
                325                 330                 335
Pro Ser Arg Asp Glu Leu Thr Lys Asn Gln Val Ser Leu Thr Cys Leu
            340                 345                 350
Val Lys Gly Phe Tyr Pro Ser Asp Ile Ala Val Glu Trp Glu Ser Asn
        355                 360                 365
Gly Gln Pro Glu Asn Asn Tyr Lys Thr Thr Pro Pro Val Leu Asp Ser
    370                 375                 380
Asp Gly Ser Phe Phe Leu Tyr Ser Lys Leu Thr Val Asp Lys Ser Arg
385                 390                 395                 400
Trp Gln Gln Gly Asn Val Phe Ser Cys Ser Val Met His Glu Ala Leu
                405                 410                 415
His Asn His Thr Thr Gln Lys Ser Leu Ser Leu Ser Pro Gly Lys Gly
            420                 425                 430
Gly Gly Gly Gly Gln Cys Asn Ala Pro Glu Trp Leu Pro Phe Ala
        435                 440                 445
Arg Pro Thr Asn Leu Thr Asp Glu Phe Glu Phe Pro Ile Gly Thr Tyr
    450                 455                 460
Leu Lys Tyr Glu Cys Arg Pro Gly Tyr Tyr Gly Arg Pro Phe Ser Ile
465                 470                 475                 480
Ile Cys Leu Lys Asn Ser Val Trp Thr Gly Ala Lys Asp Arg Cys Arg
                485                 490                 495
Arg Lys Ser Cys Arg Asn Pro Pro Asp Pro Val Asn Gly Met Val His
            500                 505                 510
Val Ile Lys Asp Ile Gln Phe Gly Ser Gln Ile Lys Tyr Ser Cys Thr
        515                 520                 525
```

```
Lys Gly Tyr Arg Leu Ile Gly Ser Ser Ser Ala Thr Cys Ile Ile Ser
        530                 535                 540

Gly Asn Thr Val Ile Trp Asp Asn Glu Thr Pro Ile Cys Asp Arg Ile
545                 550                 555                 560

Pro Cys Gly Leu Pro Pro Thr Ile Thr Asn Gly Asp Phe Ile Ser Thr
                565                 570                 575

Asn Arg Glu Asn Phe His Tyr Gly Ser Val Val Thr Tyr Arg Cys Asn
            580                 585                 590

Pro Gly Ser Gly Gly Arg Lys Val Phe Glu Leu Val Gly Glu Pro Ser
        595                 600                 605

Ile Tyr Cys Thr Ser Asn Asp Asp Gln Val Gly Ile Trp Ser Gly Pro
    610                 615                 620

Ala Pro Gln Cys Ile
625

<210> SEQ ID NO 2
<211> LENGTH: 1887
<212> TYPE: DNA
<213> ORGANISM: Artificial sequence
<220> FEATURE:
<223> OTHER INFORMATION: Synthetic sequence

<400> SEQUENCE: 2
```

| | | | | | |
|---|---|---|---|---|---|
| gacactggaa | gacctttgt | tgaaatgtat | tctgaaattc | ctgaaattat | tcatatggcc | 60 |
| gaaggaagag | aacttgttat | tccttgtaga | gttacttctc | ctaatattac | tgttactctt | 120 |
| aagaagtttc | ctcttgatac | tcttattcct | gatggaaaga | gaattatttg | ggattctaga | 180 |
| aagggattta | ttatttctaa | tgctacttat | aaggaaattg | gacttcttac | ttgtgaaaac | 240 |
| actgttaatg | gacatcttta | taagactaat | tatcttactc | atagacaaac | taataccatc | 300 |
| atcgacgtgg | ttctgagtcc | gtctcatgga | attgaactat | ctgttggaga | aaagcttgtc | 360 |
| ttaaattgta | cagcaagaac | tgaactaaat | gtggggattg | acttcaactg | gaatacccct | 420 |
| tcttcgaagc | atcagcataa | gaaacttgta | aaccgagacc | taaaaaccca | gtctgggagt | 480 |
| gagatgaaga | aattcttgag | caccctgact | atagatggtg | taacccggag | tgaccaagga | 540 |
| ttgtacaccct | gtgcagcatc | cagtgggctg | atgaccaaga | agaacagcac | atttgtcagg | 600 |
| gtccatgaaa | aagacaaaac | tcacacatgt | ccaccgtgtc | cagcacctga | actcctggtc | 660 |
| ggaccgtcag | tcttcctctt | cccccaaaa | cccaaggaca | ccctcatgat | ctcccggacc | 720 |
| cctgaggtca | catgcgtggt | ggtggacgtg | agccacgaag | accctgaggt | caagttcaac | 780 |
| tggtacgtgg | acggcgtgga | ggtgcataat | gccaagacaa | agccgcggga | ggagcagtac | 840 |
| aacagcacgt | accgtgtggt | cagcgtcctc | accgtcctgc | accaggactg | gctgaatggc | 900 |
| aaggagtaca | agtgcaaggt | ctccaacaaa | gccctcccag | cccccatcga | gaaaaccatc | 960 |
| tccaaagcca | aagggcagcc | ccgagaacca | caggtgtaca | ccctgccccc | atcccgggat | 1020 |
| gagctgacca | agaaccaggt | cagcctgacc | tgcctggtca | aaggcttcta | tcccagcgac | 1080 |
| atcgccgtgg | agtgggagag | caatgggcag | ccggagaaca | actacaagac | cacgcctccc | 1140 |
| gtgctggact | ccgacggctc | cttcttcctc | tacagcaagc | tcaccgtgga | caagagcagg | 1200 |
| tggcagcagg | ggaacgtctt | ctcatgctcc | gtgatgcatg | aggctctgca | caaccacacg | 1260 |
| acgcagaaga | gcctctccct | gtctccgggt | aaaggtggag | gaggcggtgg | tcaatgcaat | 1320 |
| gccccagaat | ggcttccatt | tgccaggcct | accaacctaa | ctgatgaatt | tgagtttccc | 1380 |
| attgggacat | atctgaaata | tgaatgccgc | cctggttatt | acggaagacc | gttttctatc | 1440 |

-continued

```
atctgcctaa aaaactcagt ctggactggt gctaaggaca ggtgcagacg taaatcatgt    1500
cgtaatcctc cagatcctgt gaatggcatg gtgcatgtga tcaaagacat ccagttcgga    1560
tcccaaatta aatattcttg tactaaagga taccgactca ttggttcctc gtctgccaca    1620
tgcatcatct caggtaatac tgtcatttgg gataatgaaa cacctatttg tgacagaatt    1680
ccttgtgggc taccccccac catcaccaat ggagatttca ttagcaccaa cagagagaat    1740
tttcactatg gatcagtggt gacctaccgc tgcaatcctg gaagcggagg gagaaaggtg    1800
tttgagcttg tgggtgagcc ctccatatac tgcaccagca atgacgatca agtgggcatc    1860
tggagcggcc ccgcacctca gtgcatt                                        1887
```

<210> SEQ ID NO 3
<211> LENGTH: 1947
<212> TYPE: DNA
<213> ORGANISM: Artificial sequence
<220> FEATURE:
<223> OTHER INFORMATION: fusion protein
<220> FEATURE:
<221> NAME/KEY: CDS
<222> LOCATION: (1)..(1947)

<400> SEQUENCE: 3

```
atg gag aca gac aca ctc ctg cta tgg gta ctg ctg ctc tgg gtt cca       48
Met Glu Thr Asp Thr Leu Leu Leu Trp Val Leu Leu Leu Trp Val Pro
1               5                   10                  15 ggg tcg act ggc gac act gga aga cct ttt gtt gaa atg tat tct gaa       96
Gly Ser Thr Gly Asp Thr Gly Arg Pro Phe Val Glu Met Tyr Ser Glu
                20                  25                  30 att cct gaa att att cat atg act gaa gga aga gaa ctt gtt att cct      144
Ile Pro Glu Ile Ile His Met Thr Glu Gly Arg Glu Leu Val Ile Pro
            35                  40                  45 tgt aga gtt act tct cct aat att act gtt act ctt aag aag ttt cct      192
Cys Arg Val Thr Ser Pro Asn Ile Thr Val Thr Leu Lys Lys Phe Pro
        50                  55                  60 ctt gat act ctt att cct gat gga aag aga att att tgg gat tct aga      240
Leu Asp Thr Leu Ile Pro Asp Gly Lys Arg Ile Ile Trp Asp Ser Arg
65                  70                  75                  80 aag gga ttt att att tct aat gct act tat aag gaa att gga ctt ctt      288
Lys Gly Phe Ile Ile Ser Asn Ala Thr Tyr Lys Glu Ile Gly Leu Leu
                85                  90                  95 act tgt gaa gct act gtt aat gga cat ctt tat aag act aat tat ctt      336
Thr Cys Glu Ala Thr Val Asn Gly His Leu Tyr Lys Thr Asn Tyr Leu
            100                 105                 110 act cat aga caa act aat acc atc atc gac gtg gtt ctg agt ccg tct      384
Thr His Arg Gln Thr Asn Thr Ile Ile Asp Val Val Leu Ser Pro Ser
        115                 120                 125 cat gga att gaa cta tct gtt gga gaa aag ctt gtc tta aat tgt aca      432
His Gly Ile Glu Leu Ser Val Gly Glu Lys Leu Val Leu Asn Cys Thr
    130                 135                 140 gca aga act gaa cta aat gtg ggg att gac ttc aac tgg gaa tac cct      480
Ala Arg Thr Glu Leu Asn Val Gly Ile Asp Phe Asn Trp Glu Tyr Pro
145                 150                 155                 160 tct tcg aag cat cag cat aag aaa ctt gta aac cga gac cta aaa acc      528
Ser Ser Lys His Gln His Lys Lys Leu Val Asn Arg Asp Leu Lys Thr
                165                 170                 175 cag tct ggg agt gag atg aag aaa ttc ttg agc acc ctg act ata gat      576
Gln Ser Gly Ser Glu Met Lys Lys Phe Leu Ser Thr Leu Thr Ile Asp
            180                 185                 190 ggt gta acc cgg agt gac caa gga ttg tac acc tgt gca gca tcc agt      624
```

```
                    Gly Val Thr Arg Ser Asp Gln Gly Leu Tyr Thr Cys Ala Ser Ser
                                195                 200                 205 ggg ctg atg acc aag aag aac agc aca ttt gtc agg gtc cat gaa aaa        672
Gly Leu Met Thr Lys Lys Asn Ser Thr Phe Val Arg Val His Glu Lys
        210                 215                 220 gac aaa act cac aca tgt cca ccg tgt cca gca cct gaa ctc ctg ggt        720
Asp Lys Thr His Thr Cys Pro Pro Cys Pro Ala Pro Glu Leu Leu Gly
225                 230                 235                 240 gga ccg tca gtc ttc ctc ttc ccc cca aaa ccc aag gac acc ctc atg        768
Gly Pro Ser Val Phe Leu Phe Pro Pro Lys Pro Lys Asp Thr Leu Met
                245                 250                 255 atc tcc cgg acc cct gag gtc aca tgc gtg gtg gtg gac gtg agc cac        816
Ile Ser Arg Thr Pro Glu Val Thr Cys Val Val Val Asp Val Ser His
        260                 265                 270 gaa gac cct gag gtc aag ttc aac tgg tac gtg gac ggc gtg gag gtg        864
Glu Asp Pro Glu Val Lys Phe Asn Trp Tyr Val Asp Gly Val Glu Val
                275                 280                 285 cat aat gcc aag aca aag ccg cgg gag gag cag tac aac agc acg tac        912
His Asn Ala Lys Thr Lys Pro Arg Glu Glu Gln Tyr Asn Ser Thr Tyr
        290                 295                 300 cgt gtg gtc agc gtc ctc acc gtc ctg cac cag gac tgg ctg aat ggc        960
Arg Val Val Ser Val Leu Thr Val Leu His Gln Asp Trp Leu Asn Gly
305                 310                 315                 320 aag gag tac aag tgc aag gtc tcc aac aaa gcc ctc cca gcc ccc atc       1008
Lys Glu Tyr Lys Cys Lys Val Ser Asn Lys Ala Leu Pro Ala Pro Ile
                325                 330                 335 gag aaa acc atc tcc aaa gcc aaa ggg cag ccc cga gaa cca cag gtg       1056
Glu Lys Thr Ile Ser Lys Ala Lys Gly Gln Pro Arg Glu Pro Gln Val
        340                 345                 350 tac acc ctg ccc cca tcc cgg gat gag ctg acc aag aac cag gtc agc       1104
Tyr Thr Leu Pro Pro Ser Arg Asp Glu Leu Thr Lys Asn Gln Val Ser
                355                 360                 365 ctg acc tgc ctg gtc aaa ggc ttc tat ccc agc gac atc gcc gtg gag       1152
Leu Thr Cys Leu Val Lys Gly Phe Tyr Pro Ser Asp Ile Ala Val Glu
        370                 375                 380 tgg gag agc aat ggg cag ccg gag aac aac tac aag acc acg cct ccc       1200
Trp Glu Ser Asn Gly Gln Pro Glu Asn Asn Tyr Lys Thr Thr Pro Pro
385                 390                 395                 400 gtg ctg gac tcc gac ggc tcc ttc ttc ctc tac agc aag ctc acc gtg       1248
Val Leu Asp Ser Asp Gly Ser Phe Phe Leu Tyr Ser Lys Leu Thr Val
                405                 410                 415 gac aag agc agg tgg cag cag ggg aac gtc ttc tca tgc tcc gtg atg       1296
Asp Lys Ser Arg Trp Gln Gln Gly Asn Val Phe Ser Cys Ser Val Met
        420                 425                 430 cat gag gct ctg cac aac cac tac acg cag aag agc ctc tcc ctg tct       1344
His Glu Ala Leu His Asn His Tyr Thr Gln Lys Ser Leu Ser Leu Ser
                435                 440                 445 ccg ggt aaa ggt gga gga ggc ggt ggt caa tgc aat gcc cca gaa tgg       1392
Pro Gly Lys Gly Gly Gly Gly Gly Gln Cys Asn Ala Pro Glu Trp
        450                 455                 460 ctt cca ttt gcc agg cct acc aac cta act gat gaa ttt gag ttt ccc       1440
Leu Pro Phe Ala Arg Pro Thr Asn Leu Thr Asp Glu Phe Glu Phe Pro
465                 470                 475                 480 att ggg aca tat ctg aaa tat gaa tgc cgc cct ggt tat tac gga aga       1488
Ile Gly Thr Tyr Leu Lys Tyr Glu Cys Arg Pro Gly Tyr Tyr Gly Arg
                485                 490                 495 ccg ttt tct atc atc tgc cta aaa aac tca gtc tgg act ggt gct aag       1536
Pro Phe Ser Ile Ile Cys Leu Lys Asn Ser Val Trp Thr Gly Ala Lys
        500                 505                 510
```

|  |  |  |  |  |  |  |  |  |  |  |  |  |  |  |  | |
|---|---|---|---|---|---|---|---|---|---|---|---|---|---|---|---|---|
| gac | agg | tgc | aga | cgt | aaa | tca | tgt | cgt | aat | cct | cca | gat | cct | gtg | aat | 1584 |
| Asp | Arg | Cys | Arg | Arg | Lys | Ser | Cys | Arg | Asn | Pro | Pro | Asp | Pro | Val | Asn | |
|  |  | 515 |  |  |  | 520 |  |  |  | 525 |  |  |  |  |  | |
| ggc | atg | gtg | cat | gtg | atc | aaa | gac | atc | cag | ttc | gga | tcc | caa | att | aaa | 1632 |
| Gly | Met | Val | His | Val | Ile | Lys | Asp | Ile | Gln | Phe | Gly | Ser | Gln | Ile | Lys | |
| 530 |  |  |  |  | 535 |  |  |  |  | 540 |  |  |  |  |  | |
| tat | tct | tgt | act | aaa | gga | tac | cga | ctc | att | ggt | tcg | tct | gcc | aca |  | 1680 |
| Tyr | Ser | Cys | Thr | Lys | Gly | Tyr | Arg | Leu | Ile | Gly | Ser | Ser | Ala | Thr |  | |
| 545 |  |  |  | 550 |  |  |  |  | 555 |  |  |  |  | 560 |  | |
| tgc | atc | atc | tca | ggt | aat | act | gtc | att | tgg | gat | aat | gaa | aca | cct | att | 1728 |
| Cys | Ile | Ile | Ser | Gly | Asn | Thr | Val | Ile | Trp | Asp | Asn | Glu | Thr | Pro | Ile | |
|  |  |  |  | 565 |  |  |  |  | 570 |  |  |  |  | 575 |  | |
| tgt | gac | aga | att | cct | tgt | ggg | cta | ccc | ccc | acc | atc | acc | aat | gga | gat | 1776 |
| Cys | Asp | Arg | Ile | Pro | Cys | Gly | Leu | Pro | Pro | Thr | Ile | Thr | Asn | Gly | Asp | |
|  |  |  | 580 |  |  |  |  | 585 |  |  |  |  | 590 |  |  | |
| ttc | att | agc | acc | aac | aga | gag | aat | ttt | cac | tat | gga | tca | gtg | gtg | acc | 1824 |
| Phe | Ile | Ser | Thr | Asn | Arg | Glu | Asn | Phe | His | Tyr | Gly | Ser | Val | Val | Thr | |
|  |  |  | 595 |  |  |  |  | 600 |  |  |  |  | 605 |  |  | |
| tac | cgc | tgc | aat | cct | gga | agc | gga | ggg | aga | aag | gtg | ttt | gag | ctt | gtg | 1872 |
| Tyr | Arg | Cys | Asn | Pro | Gly | Ser | Gly | Gly | Arg | Lys | Val | Phe | Glu | Leu | Val | |
|  | 610 |  |  |  |  | 615 |  |  |  |  | 620 |  |  |  |  | |
| ggt | gag | ccc | tcc | ata | tac | tgc | acc | agc | aat | gac | gat | caa | gtg | ggc | atc | 1920 |
| Gly | Glu | Pro | Ser | Ile | Tyr | Cys | Thr | Ser | Asn | Asp | Asp | Gln | Val | Gly | Ile | |
| 625 |  |  |  |  | 630 |  |  |  |  | 635 |  |  |  |  | 640 | |
| tgg | agc | ggc | ccc | gca | cct | cag | tgc | att |  |  |  |  |  |  |  | 1947 |
| Trp | Ser | Gly | Pro | Ala | Pro | Gln | Cys | Ile |  |  |  |  |  |  |  | |
|  |  |  |  | 645 |  |  |  |  |  |  |  |  |  |  |  | |

<210> SEQ ID NO 4
<211> LENGTH: 649
<212> TYPE: PRT
<213> ORGANISM: Artificial sequence
<220> FEATURE:
<223> OTHER INFORMATION: Synthetic sequence

<400> SEQUENCE: 4

Met Glu Thr Asp Thr Leu Leu Leu Trp Val Leu Leu Leu Trp Val Pro
1               5                   10                  15

Gly Ser Thr Gly Asp Thr Gly Arg Pro Phe Val Glu Met Tyr Ser Glu
            20                  25                  30

Ile Pro Glu Ile Ile His Met Thr Glu Gly Arg Glu Leu Val Ile Pro
        35                  40                  45

Cys Arg Val Thr Ser Pro Asn Ile Thr Val Thr Leu Lys Lys Phe Pro
    50                  55                  60

Leu Asp Thr Leu Ile Pro Asp Gly Lys Arg Ile Ile Trp Asp Ser Arg
65                  70                  75                  80

Lys Gly Phe Ile Ile Ser Asn Ala Thr Tyr Lys Glu Ile Gly Leu Leu
                85                  90                  95

Thr Cys Glu Ala Thr Val Asn Gly His Leu Tyr Lys Thr Asn Tyr Leu
            100                 105                 110

Thr His Arg Gln Thr Asn Thr Ile Ile Asp Val Val Leu Ser Pro Ser
        115                 120                 125

His Gly Ile Glu Leu Ser Val Gly Glu Lys Leu Val Leu Asn Cys Thr
    130                 135                 140

Ala Arg Thr Glu Leu Asn Val Gly Ile Asp Phe Asn Trp Glu Tyr Pro
145                 150                 155                 160

Ser Ser Lys His Gln His Lys Lys Leu Val Asn Arg Asp Leu Lys Thr
                165                 170                 175

-continued

```
Gln Ser Gly Ser Glu Met Lys Lys Phe Leu Ser Thr Leu Thr Ile Asp
            180                 185                 190
Gly Val Thr Arg Ser Asp Gln Gly Leu Tyr Thr Cys Ala Ala Ser Ser
        195                 200                 205
Gly Leu Met Thr Lys Lys Asn Ser Thr Phe Val Arg Val His Glu Lys
    210                 215                 220
Asp Lys Thr His Thr Cys Pro Pro Cys Pro Ala Pro Glu Leu Leu Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
            260                 265                 270
Glu Asp Pro Glu Val Lys Phe Asn Trp Tyr Val Asp Gly Val Glu Val
        275                 280                 285
His Asn Ala Lys Thr Lys Pro Arg Glu Glu Gln Tyr Asn Ser Thr Tyr
    290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
            340                 345                 350
Tyr Thr Leu Pro Pro Ser Arg Asp Glu Leu Thr Lys Asn Gln Val Ser
        355                 360                 365
Leu Thr Cys Leu Val Lys Gly Phe Tyr Pro Ser Asp Ile Ala Val Glu
    370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
            420                 425                 430
His Glu Ala Leu His Asn His Tyr Thr Gln Lys Ser Leu Ser Leu Ser
        435                 440                 445
Pro Gly Lys Gly Gly Gly Gly Gly Gln Cys Asn Ala Pro Glu Trp
    450                 455                 460
Leu Pro Phe Ala Arg Pro Thr Asn Leu Thr Asp Glu Phe Glu Phe Pro
465                 470                 475                 480
Ile Gly Thr Tyr Leu Lys Tyr Glu Cys Arg Pro Gly Tyr Tyr Gly Arg
                485                 490                 495
Pro Phe Ser Ile Ile Cys Leu Lys Asn Ser Val Trp Thr Gly Ala Lys
            500                 505                 510
Asp Arg Cys Arg Arg Lys Ser Cys Arg Asn Pro Pro Asp Pro Val Asn
        515                 520                 525
Gly Met Val His Val Ile Lys Asp Ile Gln Phe Gly Ser Gln Ile Lys
    530                 535                 540
Tyr Ser Cys Thr Lys Gly Tyr Arg Leu Ile Gly Ser Ser Ser Ala Thr
545                 550                 555                 560
Cys Ile Ile Ser Gly Asn Thr Val Ile Trp Asp Asn Glu Thr Pro Ile
                565                 570                 575
Cys Asp Arg Ile Pro Cys Gly Leu Pro Pro Thr Ile Thr Asn Gly Asp
            580                 585                 590
Phe Ile Ser Thr Asn Arg Glu Asn Phe His Tyr Gly Ser Val Val Thr
```

-continued

```
            595                 600                 605
Tyr Arg Cys Asn Pro Gly Ser Gly Gly Arg Lys Val Phe Glu Leu Val
            610                 615                 620

Gly Glu Pro Ser Ile Tyr Cys Thr Ser Asn Asp Asp Gln Val Gly Ile
625                 630                 635                 640

Trp Ser Gly Pro Ala Pro Gln Cys Ile
                    645
```